United States Patent [19]
Addy et al.

[11] Patent Number: 6,030,579
[45] Date of Patent: *Feb. 29, 2000

[54] METHOD OF STERILIZATION USING PRETREATMENT WITH HYDROGEN PEROXIDE

[75] Inventors: Tralance O. Addy, Coto de Caza; Paul Taylor Jacobs, Trabuco Canyon; Szu-Min Lin, Laguna Hills; Jon Morrell Jacobs, Trabuco Canyon, all of Calif.

[73] Assignee: Johnson & Johnson Medical, Inc., New Brunswick, N.J.

[*] Notice: This patent is subject to a terminal disclaimer.

[21] Appl. No.: 08/628,965

[22] Filed: Apr. 4, 1996

[51] Int. Cl.⁷ .................. A61L 2/18; A61L 2/14
[52] U.S. Cl. .................. 422/28; 422/7; 422/22; 422/23; 422/29; 422/33; 422/40; 422/292; 422/906; 220/87.1; 220/913; 210/436
[58] Field of Search .................. 422/7, 22, 23, 422/28, 29, 33, 40, 292, 906; 220/87.1, 9.3; 210/436

[56] References Cited

U.S. PATENT DOCUMENTS

| | | | |
|---|---|---|---|
| 4,169,123 | 9/1979 | Moore et al. | 422/29 |
| 4,169,124 | 9/1979 | Forstrom et al. | 422/33 |
| 4,643,876 | 2/1987 | Jacobs et al. | 422/23 |
| 4,756,882 | 7/1988 | Jacobs et al. | 422/23 |
| 4,943,414 | 7/1990 | Jacobs et al. | 422/28 |
| 4,952,370 | 8/1990 | Cummings et al. | 422/28 |
| 5,087,418 | 2/1992 | Jacob | 422/23 |
| 5,115,166 | 5/1992 | Campbell et al. | 315/111.21 |
| 5,310,524 | 5/1994 | Campbell et al. | 422/33 |
| 5,413,758 | 5/1995 | Caputo et al. | 422/22 |
| 5,451,368 | 9/1995 | Jacob | 422/23 |
| 5,492,672 | 2/1996 | Childers et al. | 422/28 |
| 5,527,508 | 6/1996 | Childers et al. | 422/33 |
| 5,534,221 | 7/1996 | Hillebrenner et al. | 422/33 |
| 5,556,607 | 9/1996 | Childers et al. | 422/300 |

FOREIGN PATENT DOCUMENTS

| | | |
|---|---|---|
| 0207417 | 1/1987 | European Pat. Off. . |
| 0223479 | 5/1987 | European Pat. Off. . |
| 0 302 419 A2 | 2/1989 | European Pat. Off. . |
| 456135 | 11/1991 | European Pat. Off. . |
| 41 02 055 A1 | 8/1991 | Germany . |

*Primary Examiner*—Elizabeth Kemmerer
*Assistant Examiner*—David S. Romeo
*Attorney, Agent, or Firm*—Knobbe, Martens, Olson & Bear, LLP

[57] ABSTRACT

A method for hydrogen peroxide vapor sterilization of medical devices and similar instruments having long narrow lumens or diffusion restricted areas includes the step of pretreating the article to be sterilized with a dilute solution of hydrogen peroxide prior to exposure to a vacuum or a vacuum followed by plasma. The method is such that, upon vaporization of the solution caused by the vacuum, the hydrogen peroxide remains in contact with the article for a time sufficient to achieve sterilization.

68 Claims, 2 Drawing Sheets

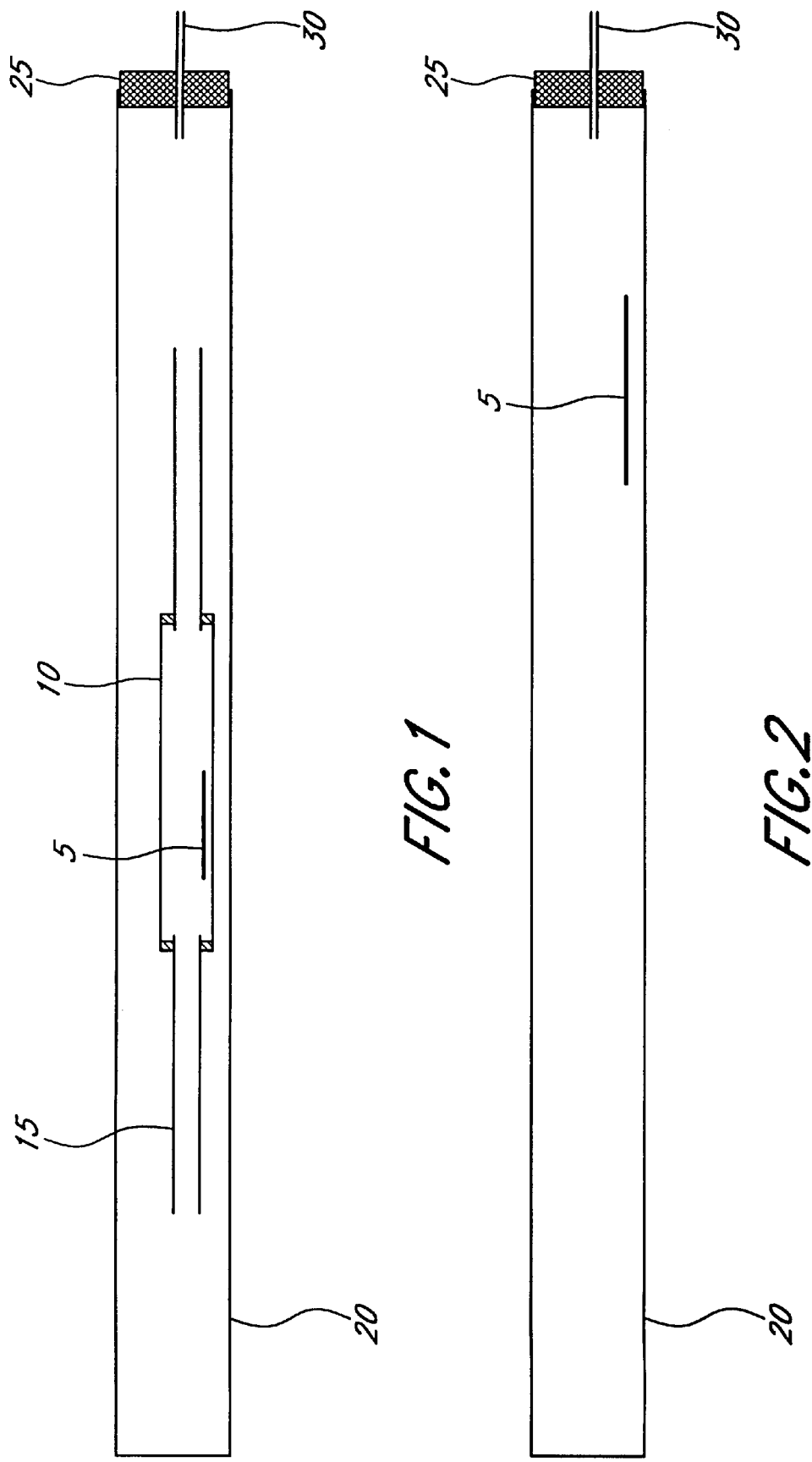

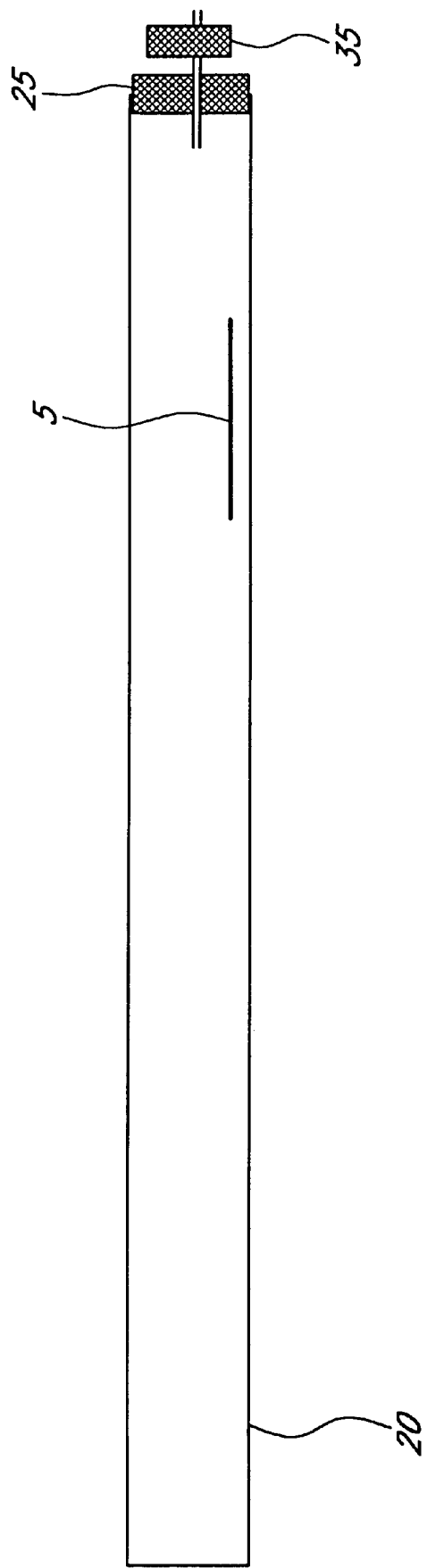

METHOD OF STERILIZATION USING PRETREATMENT WITH HYDROGEN PEROXIDE

BACKGROUND OF THE INVENTION

1. Field of the Invention

This invention relates to a process for using hydrogen peroxide and negative pressure to sterilize articles such as medical instruments, and more particularly, to a method which includes the step of pretreating the articles with liquid hydrogen peroxide prior to exposure to negative pressure or negative pressure combined with plasma.

2. Description of the Related Art

Medical instruments have traditionally been sterilized using either heat, such as is provided by steam, or a chemical, such as formaldehyde or ethylene oxide in the gas or vapor state. Each of these methods has drawbacks. Many medical devices, such as fiberoptic devices, endoscopes, power tools, etc. are sensitive to heat, moisture, or both. Formaldehyde and ethylene oxide are both toxic gases that pose a potential hazard to healthcare workers. Problems with ethylene oxide are particularly severe, because its use requires long aeration times to remove the gas from articles that have been sterilized. This makes the sterilization cycle time undesirably long.

Sterilization using liquid hydrogen peroxide solution has been found to require high concentration of sterilant, extended exposure time and/or elevated temperatures. However, sterilization using hydrogen peroxide vapor has been shown to have some advantages over other chemical sterilization processes (see, e.g., U.S. Pat. Nos. 4,169,123 and 4,169,124). The combination of hydrogen peroxide with a plasma provides certain additional advantages, as disclosed in U.S. Pat. No. 4,643,876, issued Feb. 17, 1987 to Jacobs et al. U.S. Pat. No. 4,756,882, issued Jul. 12, 1988 also to Jacobs et al. discloses the use of hydrogen peroxide vapor, generated from an aqueous solution of hydrogen peroxide, as a precursor of the reactive species generated by a plasma generator. The combination of hydrogen peroxide vapor diffusing into close proximity with the article to be sterilized and plasma acts to sterilize the articles, even within closed packages. Further, these methods of combining hydrogen peroxide vapor with a plasma, while useful in "open" systems, have been found to be inadequate to effect sterilization in articles having diffusion-restricted areas, since the methods are dependent upon diffusion of the sterilant vapor into close proximity with the article before sterilization can be achieved. Thus, these methods have been found to require high concentration of sterilant, extended exposure time and/or elevated temperatures when used on long, narrow lumens. For example, lumens longer than 27 cm and/or having an internal diameter of less than 0.3 cm have been particularly difficult to sterilize. Thus, no simple, safe, effective method of sterilizing smaller lumens exists in the prior art.

The sterilization of articles containing diffusion-restricted areas, such as long narrow lumens, therefore presents a special challenge. Methods that use hydrogen peroxide vapor that has been generated from an aqueous solution of hydrogen peroxide have certain disadvantages, because:

1. Water has a higher vapor pressure than hydrogen peroxide and will vaporize faster than hydrogen peroxide from an aqueous solution.

2. Water has a lower molecular weight than hydrogen peroxide and will diffuse faster than hydrogen peroxide in the vapor state.

Because of this, when an aqueous solution of hydrogen peroxide is vaporized in the area surrounding the items to be sterilized, the water reaches the items first and in higher concentration. The water vapor therefore becomes a barrier to the penetration of hydrogen peroxide vapor into diffusion restricted areas, such as small crevices and long narrow lumens. One cannot solve the problem by removing water from the aqueous solution and using more concentrated hydrogen peroxide, since, among other reasons, concentrated solutions of hydrogen peroxide greater than 65% by weight can be hazardous due to the oxidizing nature thereof.

U.S. Pat. No. 4,952,370 to Cummings et al. discloses a sterilization process wherein aqueous hydrogen peroxide vapor is first condensed on the article to be sterilized, and then a source of vacuum is applied to the sterilization chamber to evaporate the water and hydrogen peroxide from the article. This method is suitable to sterilize surfaces, however, it is ineffective at rapidly sterilizing diffusion-restricted areas, such as those found in lumened devices, since it too depends on the diffusion of the hydrogen peroxide vapor into the lumen to effect sterilization.

U.S. Pat. No. 4,943,414, entitled "Method for Vapor Sterilization of Articles Having Lumens," and issued to Jacobs et al., discloses a process in which a vessel containing a small amount of a vaporizable liquid sterilant solution is attached to a lumen, and the sterilant vaporizes and flows directly into the lumen of the article as the pressure is reduced during the sterilization cycle. This system has the advantage that the water and hydrogen peroxide vapor are pulled through the lumen by the pressure differential that exists, increasing the sterilization rate for lumens, but it has the disadvantage that the vessel needs to be attached to each lumen to be sterilized. In addition, water is vaporized faster and precedes the hydrogen peroxide vapor into the lumen.

In U.S. Pat. No. 5,492,672, there is disclosed a process for sterilizing narrow lumens. This process uses a multicomponent sterilant vapor and requires successive alternating periods of flow of sterilant vapor and discontinuance of such flow. A complex apparatus is used to accomplish the method. Because flow through of vapor is used, closed end lumens are not readily sterilized in the process.

Thus, there remains a need for a simple and effective method of vapor sterilization of articles having areas where diffusion of these vapors is restricted, such as long, narrow lumens.

SUMMARY OF THE INVENTION

One aspect of the present invention relates to a method for sterilizing an interior of a device with a diffusion restricted area, such as a device having a lumen. The method includes the steps of contacting the interior of the device with a liquid solution comprising hydrogen peroxide, and exposing the device to negative pressure for a time period sufficient to effect complete sterilization. In one embodiment, the liquid solution is peracetic acid. If the exposing step is conducted for 1 hour at 40° C. and 10 torr, the diffusion restricted area preferably retains 0.17 mg/L or more hydrogen peroxide, or retains 17% or more of the hydrogen peroxide placed therein after the exposing step. In certain preferred embodiments, the diffusion-restricted area has the same or more diffusion restriction than provided by a lumen 27 cm in length and an internal diameter of 3 mm, or has the same or more diffusion restriction than provided by a lumen having a ratio of length to internal diameter greater than 50. The solution is preferably at a concentration of less than 25% by weight. The contacting step can be performed by delivery via a method such as injection, static soak, liquid flow-through or aerosol spray. In a preferred embodiment, the diffusion-restricted area is a lumen at least 27 cm in length and having an internal diameter of no more than 3 mm, more preferably having an internal diameter of no more than 1 mm. The exposing step is preferably performed for 60 minutes or less, and is preferably performed at a pressure less than the vapor pressure of hydrogen peroxide. Thus, the preferred pressure range under conditions of the present invention is between 0 and 100 torr. In one particularly preferred embodiment, the pressure is approximately 10 torr and the exposing step is conducted at a temperature of approximately 23° C. to approximately 28° C. The exposing step can include the step of heating the article, such as by heating the chamber in which the exposing step occurs. The chamber can be heated to about 40° C. to about 45° C. Alternatively, the solution can be heated, such as to a temperature of about 40° C. to about 45° C. Optionally, the step of exposing the device to a plasma can be conducted during the step of exposing the device to negative pressure. In one embodiment employing exposure to plasma, the method is performed within a first chamber and the plasma is generated in a second, separate chamber. This embodiment further comprises the step of flowing the plasma into the first chamber. Advantageously, the contacting and/or exposing steps of the method can be repeated one or more times.

Another aspect of the present invention relates to a method for sterilizing an interior and an exterior of an article. This method includes the following steps: contacting the article with a liquid solution comprising hydrogen peroxide; and placing the article in a diffusion-restricted environment. The contacting and placing steps can be performed in either order. These steps are followed by exposing the diffusion-restricted environment to negative pressure for a time period sufficient to effect complete sterilization. The contacting step can be performed both before and after the placing step. If the exposing step is conducted at 40° C. and 10 torr, the diffusion restricted environment preferably retains 0.17 mg/L or more hydrogen peroxide after the exposing step, or retains 17% or more of the hydrogen peroxide placed therein after the exposing step. The exposing step can include the step of heating the article, such as by heating the chamber in which the exposing step occurs or by heating the liquid solution. In certain preferred embodiments, the diffusion-restricted environment has the same or more diffusion restriction than provided by a single entry/exit port of 9 mm or less in internal diameter and 1 cm or greater in length, or is sufficiently diffusion restricted to completely sterilize a stainless steel blade within a 2.2 cm by 60 cm glass tube having a rubber stopper with a 1 mm by 50 cm stainless steel exit tube therein at a vacuum of 10 torr for one hour at 40° C. The solution can be peracetic acid. The contacting step can be by delivery via a method such as injection, static soak, liquid flow-through or aerosol spray. Plasma can also be used during the step of exposing the lumen to negative pressure. If plasma is used, the method can be performed within a sealed chamber and the plasma generated within the container. Thus, the method can be performed within a first chamber and the plasma generated in a second, separate chamber and the plasma flowed into the first chamber. The diffusion-restricted container can have at least one exit tube, such as one that is at least 1.0 cm in length and has an internal diameter of 9 mm or less. The exit tube can also include a filter. In a preferred embodiment, the filter is sufficient to prevent entry of bacteria from the environment into the container. The solution can be used at a concentration of less than 25% by weight. The exposing step is preferably performed for 60 minutes or less. The method can be conducted along with the step of heating the article during the exposing step. Thus, the exposing step can be conducted within a chamber, and the chamber heated during the exposing step. The exposing step can be conducted at a negative pressure between 0 and 100 Torr. Advantageously, the various steps of this method can also be repeated one or more times.

Still one more aspect of the invention relates to a method for making a sterilized article within a diffusion-restricted container. This method includes contacting the article with a solution comprising hydrogen peroxide, and placing the article in the diffusion-restricted container in either order. If the initial contacting step precedes the placing step, the contacting step can be repeated after the placing step. These steps are followed by exposing the diffusion-restricted container to negative pressure for a time period sufficient to effect complete sterilization of the article. The container used in this aspect of the invention has at least one exit tube. The exit tube preferably has a filter therein which is preferably sufficient to prevent entry of bacteria into the container. The exit tube is at least 1.0 cm in length and/or has an internal diameter of 9 mm or less. The solution used can be peracetic acid. Advantageously, the exposing step, the contacting step, or the entire method can be repeated one or more times. In a preferred embodiment, the contacting step comprises delivery via injection, static soak, liquid flow-through or aerosol spray. The container can be exposed to a plasma during the step of exposing the container to negative pressure. In one embodiment, the method is performed within a sealed chamber and the plasma is generated within the chamber. The exposing step is preferably performed for 60 minutes or less and/or at a pressure between 0 and 100 Torr. The container can be heated during the exposing step, or the solution heated prior to the contacting step. The invention also includes the sterilized article within a diffusion-restricted container produced by the method of this aspect.

BRIEF DESCRIPTION OF THE DRAWINGS

FIG. 1 is a cross-sectional illustration of a lumen containing an inoculated stainless steel blade placed within a glass tube having only a narrow opening to create a diffusion-restricted environment for testing the sterilization method of the present invention.

FIG. 2 is a cross-sectional illustration of an inoculated stainless steel blade placed directly within a glass tube having only a narrow opening to create an alternate diffusion-restricted environment for testing the sterilization method of the present invention.

FIG. 3 is a cross-sectional illustration of an inoculated stainless steel blade placed directly within a glass tube having a filter placed at its narrow opening to create an alternate diffusion-restricted environment for testing the sterilization method of the present invention.

DETAILED DESCRIPTION OF THE PREFERRED EMBODIMENT

Sterilizing the inside of lumened devices has always posed a challenge to sterilization systems. Achieving rapid sterilization of lumened devices or other diffusion restricted articles at low temperatures and low concentrations of sterilant represents an even greater challenge. In the present invention, the shortcomings of the prior art sterilization systems are overcome by pretreating articles to be sterilized with an aqueous solution of hydrogen peroxide (i.e. a solution comprising both water and hydrogen peroxide) prior to exposure to a vacuum, or optionally, plasma. The method of the present invention provides for the rapid sterilization of lumened and non-lumened articles under conditions that will not damage the articles nor leave toxic residues on the sterile articles.

In the method of the present invention, dilute, aqueous solutions of hydrogen peroxide are delivered into direct contact with the article to be sterilized. In the case of a lumened device, the solution is delivered directly into the lumen. In the case of an article having an area where diffusion of vapor is restricted, the solution is delivered to the interior of the diffusion restricted area. The hydrogen peroxide solution is delivered into the lumen or into contact with the article to be sterilized through means such as direct delivery, a static soaking process, a liquid flow-through process, or by aerosol spray. The aqueous solutions of hydrogen peroxide can be relatively dilute, e.g., as low as 1–3% or lower by weight, since sterilization is not achieved through contact with the hydrogen peroxide solution, but rather, is achieved at low temperatures and in short periods of time upon exposure to hydrogen peroxide vapor under vacuum or vacuum combined with plasma. The method of the present invention is particularly effective with articles having inaccessible or hard-to-reach places. Such articles include long, narrow lumens, hinges, and other articles having spaces where diffusion of vapors is restricted.

The general operation of one embodiment of the method of the present invention, which is useful for sterilizing the inside of long, narrow lumens, is as follows:

1. The lumen to be sterilized is exposed to an aqueous solution of dilute hydrogen peroxide. The aqueous solution can be delivered as a small amount directly into the lumen, or by static soaking, liquid flow-through, or aerosol spray.

2. The lumen to be sterilized is placed within a chamber, and the chamber is sealed and evacuated. (Peroxide can also be delivered to the inside of the article after placing the article in the chamber.)

3. The lumen is exposed to the vacuum for a period of time and at a temperature sufficient to effect sterilization.

4. The sterile lumen is removed from chamber.

In an alternative embodiment of the method of the present invention, a similar method is used to sterilize both the inside and outside of an article. In this alternative embodiment, the article to be sterilized is placed in a diffusion-restricted environment. If the article to be sterilized is itself diffusion-restricted, such as a long, narrow lumen, peroxide is introduced to the inside of the article. For articles which are not diffusion-restricted, peroxide can be introduced anywhere into the diffusion-restricted environment. Peroxide can be introduced either before or after placing the article in the diffusion-restricted environment. The diffusion-restricted environment containing the article to be sterilized is then placed in the chamber, exposed to vacuum and removed as in steps 2 through 4 above.

In yet another alternative embodiment of the present invention, the article to be sterilized is exposed to a vacuum followed by low temperature plasma for a time sufficient to effect sterilization. When used in the present specification and claims, the term "plasma" is intended to include any portion of the gas or vapor that contains electrons, ions, free radicals, dissociated and/or excited atoms or molecules produced as a result of an applied electric field, including any accompanying radiation that might be produced. The applied field may cover a broad frequency range; however, a radio frequency or microwaves are commonly used.

The sterilization method of the present invention can also be used with plasmas generated by the method disclosed in the previously mentioned U.S. Pat. No. 4,643,876. Alternatively, it may be used with plasmas described in U.S. Pat. Nos. 5,115,166 or 5,087,418, in which the article to be sterilized is located in a chamber that is separated from the plasma source.

The present invention provides several advantages over earlier vapor sterilization systems, such as, (1) the rapid sterilization of lumened devices and diffusion restricted articles can be rapidly achieved at low temperatures; (2) the use of concentrated, potentially hazardous, solutions of anti-microbials is avoided; (3) the need to attach a special vessel to deliver sterilant vapors into long, narrow lumens is eliminated; (4) no toxic residues remain; (5) since the product is dry at the end of the process, sterile storage of these articles can be achieved; (6) closed end lumens can be sterilized; and (7) the process can be repeated as desired without undue effects. The method of the present invention therefore provides for a highly efficient, nonhazardous, and relatively inexpensive method of sterilization.

To determine the efficacy of the sterilization method of the present invention, preliminary tests were first performed to evaluate the effect of dilute hydrogen peroxide solutions on contaminated surfaces in an open, non-diffusion restricted environment. These tests are described below in Example 1.

EXAMPLE 1

To evaluate the sterilization efficacy of dilute hydrogen peroxide solution alone, a biological challenge consisting of $2.5 \times 10^6$ *Bacillus stearothermophilus* spores on a stainless steel scalpel blade was used. Inoculated blades were submerged in 40 ml of hydrogen peroxide solution in a 100 ml beaker. Four different concentrations of hydrogen peroxide solution were used: 3%, 6%, 9% and 12% by weight. The blades were allowed to soak in the peroxide solutions for various time periods. The blades were then removed from the solution and tested for sterility. The results of this testing are listed in Table 1 as a ratio of the number of inoculated blades which remain contaminated after treatment over the number of inoculated blades tested.

TABLE 1

Effect of $H_2O_2$ Concentration and Soak Times on Sporicidal Activity of $H_2O_2$ Solution

| | Concentration of $H_2O_2$ Solution | | | |
|---|---|---|---|---|
| Soak Time | 3% | 6% | 9% | 12% |
| 1 min | 4/4 | 4/4 | 4/4 | 4/4 |
| 5 min | 4/4 | 4/4 | 4/4 | 4/4 |
| 30 min | 4/4 | 4/4 | 4/4 | 4/4 |
| 60 min | 4/4 | 4/4 | 4/4 | 4/4 |
| 90 min | N/D* | 4/4 | 2/4 | 0/4 |
| 120 min | N/D | 4/4 | N/D | N/D |

*N/D = not determined

Complete sterilization was not effected until after the blades had been soaked in 12% hydrogen peroxide solution for at least 90 minutes. Moreover, none of the blades tested were sterilized after 2 hours in 6% hydrogen peroxide solution. It is clear from these data that contact with dilute hydrogen peroxide solution alone is ineffective at providing sterilization, unless extended soak times and concentrated solutions are used.

Testing was next performed to evaluate the effect on the sterilization of long, narrow lumens of a pretreatment step in which the lumens to be sterilized are exposed to hydrogen peroxide solution prior to exposure to a vacuum. The testing evaluated the efficacy of hydrogen peroxide vapor sterilization inside the lumens.

The testing is detailed below in Example 2.

EXAMPLE 2

A biological challenge consisting of $1.9 \times 10^6$ B. stearothermophilus spores on a stainless steel scalpel blade was used. Some inoculated blades were pretreated with a solution of aqueous hydrogen peroxide. Other inoculated blades, designated control blades, did not receive pretreatment with hydrogen peroxide. The pretreatment consisted of 5 minutes of static soaking in peroxide solution. The pretreated blades were blotted dry, and each blade was then placed inside a stainless steel lumen, 3 mm internal diameter (ID)×50 cm length. The lumen had a center piece of 1.3 cm ID and 5 cm length. The pretreated blade was placed inside this center piece, and additional hydrogen peroxide solution was added into the center piece in various amounts. Control blades were handled identically, except that they did not receive pretreatment with hydrogen peroxide solution. The lumens were placed in a vacuum chamber, and the chamber was evacuated to 1 Torr and held there for 15 minutes, during which time the temperature increased from approximately 23° C. to approximately 28° C. Following exposure to the vacuum, the chamber was vented and the blades were removed from the chamber and tested for sterility. The results were as follows:

TABLE 2

Effect of Pretreatment and Hydrogen Peroxide Concentration on Sterilization of the Interior of Lumens

| Additional peroxide added into the center piece | Blades not pretreated with peroxide | Blades pretreated in peroxide solution |
|---|---|---|
| (A) With 1% hydrogen peroxide solution and vacuum | | |
| 10 μL | + | + |
| 20 μL | + | + |
| 30 μL | + | + |
| 40 μL | + | + |
| 50 μL | + | + |
| 100 μL | + | . |
| 150 μL | + | . |
| 200 μL | . | . |
| 250 μL | . | . |
| (B) With 3% hydrogen peroxide solution and vacuum | | |
| 10 μL | . | . |
| 20 μL | . | . |
| 30 μL | . | . |
| 40 μL | . | . |
| 50 μL | . | . |
| 100 μL | . | . |
| 150 μL | . | . |
| 200 μL | . | . |
| 250 μL | . | . |
| (C) With 6% hydrogen peroxide solution and vacuum | | |
| 10 μL | . | . |
| 20 μL | . | . |
| 30 μL | . | . |
| 40 μL | . | . |
| 50 μL | . | . |

As seen from these results, sterilization can be effected using relatively dilute solutions of peroxide and exposure to negative pressure. When the vacuum was applied, the peroxide added to the center piece of the lumen was vaporized and contacted the blade, which was sufficient to effect sterilization. It can be seen from these data that the pretreatment increases effectiveness, but that pre-treatment is unnecessary as long as the peroxide diffuses from the inside to the outside.

Sterilization inside various lumen sizes after pretreatment with peroxide was compared with sterilization inside the lumens without the pretreatment step. This testing is detailed in Example 3.

EXAMPLE 3

A biological challenge consisting of $1.9 \times 10^6$ B. stearothermophilus spores on a stainless steel scalpel blade was used. Test A in Table 3 below consisted of the inoculated blades being pretreated with a solution of 3% aqueous hydrogen peroxide. The pretreatment consisted of 5 minutes of static soaking in the peroxide solution. The pretreated blades were blotted dry, then placed into the center piece of a stainless steel lumen which varied in size, together with 10 μl of 3% hydrogen peroxide solution. The center piece was 1.3 cm ID and 5 cm length. Test B in Table 3 below consisted of identically inoculated control blades which did not receive pretreatment with hydrogen peroxide. Each inoculated control blade was placed directly into the center piece of a stainless steel lumen together with 10 μl of 3% hydrogen peroxide solution. The center piece had dimensions identical to those in Test A. Lumens of various dimensions were used to evaluate the effect on sterilization of lumen internal diameter and length. The lumens were placed in a vacuum chamber, and the chamber was evacuated to 1 Torr for 15 minutes. During this 15 minutes of the sterilization cycle, the temperature increased from approximately 23° C. to approximately 28° C. Following exposure to the vacuum, the chamber was vented and the blades were removed from the chamber and tested for sterility. The results are reported in Table 3, where "L/D Ratio" indicates the ratio of length to internal diameter.

TABLE 3

Effect of Pretreatment With Dilute Hydrogen Peroxide in Various Sized Lumens

| SS lumen size | L/D Ratio | Test A | Test B |
|---|---|---|---|
| 1 mm × 50 cm | 500 | − | − |
| 1 mm × 40 cm | 400 | − | − |
| 1 mm × 27 cm | 270 | − | − |
| 1 mm × 15 cm | 150 | − | − |
| 3 mm × 50 cm | 166⅔ | − | − |
| 3 mm × 40 cm | 133⅓ | − | − |
| 3 mm × 27 cm | 90 | − | + |
| 3 mm × 15 cm | 50 | + | + |
| 6 mm × 50 cm | 83⅓ | − | − |
| 6 mm × 40 cm | 66⅔ | − | − |
| 6 mm × 27 cm | 45 | + | + |
| 6 mm × 15 cm | 25 | + | + |

All lumens having a L/D ratio greater than 50 which were tested under the conditions of Test A of Example 3 were sufficiently diffusion-restricted to be sterilized in this system. Thus, it is believed that other lumens having an L/D ratio greater than 50 should also provide a sufficient level of diffusion-restriction for sterilization in accordance with the present invention. This testing shows that, in direct contrast to prior art methods, sterility through diffusion of hydrogen peroxide vapor from inside the article to outside the article is easier to achieve in longer, narrower lumens than in shorter, wider lumens. This is believed to be due to the larger lumens allowing too much of the hydrogen peroxide vapor to diffuse out of the inside of the lumen during the sterilization process. Thus, the vapor does not contact the internal surfaces for a period of time sufficient or at a concentration sufficient to effect sterilization.

As discussed above, prior art methods of hydrogen peroxide vapor sterilization of lumens are generally limited to use on relatively short and wide lumens. In contrast to these prior art methods, the method of the present invention is effective on the interior of long, narrow lumens, including those longer than 27 cm in length and/or having an internal diameter of less than 3 mm.

To determine whether the ability of the sterilant vapor to diffuse within the system is a critical factor in achieving sterility, additional testing was performed to compare diffusion restricted and open, non-diffusion restricted systems. A non-diffusion restricted system is one in which the diffusion of vapors in and around the article is not restricted by narrow openings, long, narrow lumens, or the like. As used herein, "diffusion-restricted" refers to any one or more of the following properties: (1) the ability of an article placed within the sterilization system of the present invention to retain 0.17 mg/L or more hydrogen peroxide solution after one hour at 40° C. and 10 torr; (2) having the same or more diffusion restriction than provided by a single entry/exit port of 9 mm or less in internal diameter and 1 cm or greater in length; (3) having the same or more diffusion restriction than provided by a lumen 27 cm in length and having an internal diameter of 3 mm; (4) having the same or more diffusion restriction than provided by a lumen having a ratio of length to internal diameter greater than 50; (5) the ability of an article placed within the sterilization system of the present invention to retain 17% or more of the hydrogen peroxide solution placed therein after one hour at 40° C. and 10 torr; or (6) being sufficiently diffusion-restricted to completely sterilize a stainless steel blade within a 2.2 cm by 60 cm glass tube having a rubber stopper with a 1 mm by 50 cm stainless steel exit tube therein at a vacuum of 10 torr for one hour at 40° C. in accordance with the present invention. It is acknowledged that characteristics (1) and (5) will vary depending on the initial concentration of hydrogen peroxide placed into the article; however, this can be readily determined by one having ordinary skill in the art.

As discussed in the Background of the Invention, articles having diffusion restricted areas are difficult to sterilize using known methods of hydrogen peroxide vapor sterilization, since these methods are dependent upon the diffusion of peroxide vapors from outside the article to the interior of the article. Testing performed to evaluate the importance of sterilant vapor diffusion is described in Example 4.

EXAMPLE 4

Hydrogen peroxide vapor sterilization was tested in both open and diffusion restricted systems. The open system consisted of stainless steel lumens having internal diameters of 1, 3, and 6 mm, and lengths of 15, 27, 40 and 50 cm. Stainless steel scalpel blades were inoculated with $1.9 \times 10^6$ *B. stearothermophilus* spores, and the blades placed in the center piece of the lumen together with 10 µl of 3% hydrogen peroxide solution. The dimensions of the center piece were 1.3 cm ID, 5 cm length and 6.6 cc volume.

The diffusion restricted system is illustrated in FIG. 1. Identically inoculated scalpel blades 5 were placed within the center pieces 10 of lumens 15 having dimensions identical to those described above. Ten µl of 3% hydrogen peroxide solution was also added to the center piece 10 of the lumen 15. The lumen 15 was then placed within a 2.2 cm×60 cm glass tube 20. The tube 20 was closed at one end, and the open end was plugged with a rubber stopper 25 having a 1 mm×10 cm stainless steel tube 30 inserted through the stopper 25. Thus, gases entering or exiting the glass tube 20 could pass only through this 1 mm×10 cm opening.

The open lumen system and the diffusion restricted system were placed inside a vacuum chamber. The chamber was evacuated to 1 Torr pressure and held there for 15 minutes, during which time the temperature increased from approximately 23° C. to approximately 28° C. The chamber was then vented, and the blades removed from the lumens and tested for sterility. The results are as follows:

TABLE 4

Hydrogen Peroxide Vapor Sterilization
in Open and Diffusion Restricted Systems

| System | Peroxide amount | Length | 1 mm ID | 3 mm ID | 6 mm ID |
|---|---|---|---|---|---|
| Open | 10 µL of 3% | 50 cm | – | – | – |
| | | 40 cm | – | – | – |
| | | 27 cm | – | + | + |
| | | 15 cm | – | + | + |
| Diffusion Restricted Environment | 10 µL of 3% | 50 cm | – | – | – |
| | | 40 cm | – | – | – |
| | | 27 cm | – | – | – |
| | | 15 cm | – | – | – |

Under the test conditions of Example 4, sterilization was not achieved in the shorter, wider lumens in the open system without pre-treatment with hydrogen peroxide. Pre-treatment, and other test conditions, such as higher peroxide concentration or longer treatment time, would likely allow sterilization of the 27 cm×3 mm lumen, which has an L/D ratio greater than 50. In the diffusion restricted system, the blades were sterilized in all sizes of lumens, using a 3% hydrogen peroxide solution.

These results indicate that providing a source of hydrogen peroxide within a diffusion restricted environment allows for complete sterilization within the system. It is the restriction of vapor diffusion in the system, not the length or internal diameter of the lumen per se that determines the efficacy of the hydrogen peroxide vapor sterilization. Again, however, these data show that, unlike the prior art methods of hydrogen peroxide vapor sterilization of lumens, the method of the present invention is effective even on non-diffusion-restricted articles when placed into a diffusion-restricted environment.

To further test the idea that restriction of the diffusion of vapor in a system affects the ability to sterilize the system, the following experiment was performed.

EXAMPLE 5

A stainless steel scalpel blade 5 was placed within a 2.2 cm×60 cm glass tube 20 which was closed at one end, as illustrated in FIG. 2. Each blade 5 had been inoculated with $1.9 \times 10^6$ *B. stearothermophilus* spores. For some of the testing, the glass tube 20 was left open at one end, providing an open system. To create a diffusion restricted environment, the open end of the glass tube 20 was sealed with a rubber stopper 25 having a 1 mm×10 cm stainless steel tube 30 through its center. In both the open and diffusion restricted systems, hydrogen peroxide solution at a concentration of either 3% or 6% was added to the glass tube 20 in amounts of 50, 100, 150 or 200 µl, together with the inoculated blade 5. The tube 20 was placed in a vacuum chamber, and the chamber evacuated to 1 Torr for 15 minutes, during which time the temperature increased from approximately 23° C. to approximately 28° C. The diffusion restricted system only was also tested at 1 Torr for 30 minutes, during which time the temperature increased from approximately 23° C. to approximately 33° C. The vacuum chamber was then vented, and the blades 5 removed from the tube 20 and tested for sterility. The results are listed in Table 5 below.

TABLE 5

Hydrogen Peroxide Vapor Sterilization in Open and Diffusion Restricted Systems

| | 50 µL | 100 µL | 150 µL | 200 µL |
|---|---|---|---|---|
| Open System, 15 minutes vacuum at 1 Torr: | | | | |
| 3% peroxide | + | + | + | + |
| 6% peroxide | + | + | + | + |
| Diffusion Restricted System, 15 minutes vacuum at 1 Torr: | | | | |
| 3% peroxide | + | − | − | − |
| 6% peroxide | − | − | − | − |
| Diffusion Restricted System, 30 minutes vacuum at 1 Torr: | | | | |
| 3% peroxide | − | − | − | − |

These results show that the addition of hydrogen peroxide solution, followed by exposure to vacuum, is ineffective for achieving rapid sterilization in an open system. Identical treatment in a diffusion restricted system, by comparison, results in complete sterilization, except at the very weakest concentration of hydrogen peroxide solution in an amount of only 50 µl. Sterilization can be effected, however, by increasing the exposure to the vacuum.

Thus, the method of the present invention, wherein small amounts of hydrogen peroxide solution are delivered to the article to be sterilized prior to exposure to a vacuum, is an effective method of sterilization. The method does not depend on the diffusion of sterilant vapor into the article being sterilized. Rather, the hydrogen peroxide vapor is created by the vacuum within the system. This vapor is prevented from leaving the system too quickly, because the diffusion of the sterilant vapor from the inside of the article to the outside of the article is slowed. In a diffusion restricted environment, the vapor therefore contacts the article to be sterilized for a period of time sufficient to effect complete sterilization. In addition, unlike the prior art methods where the water in the peroxide solution is vaporized first and becomes a barrier to the penetration of the peroxide vapor, the method of the present invention removes the water from the system first, thereby concentrating the hydrogen peroxide vapor remaining in the system. More importantly, in the present invention, the diffusion of vapor is from the inside to outside rather than outside to inside as in the prior art. As a result, diffusion-restriction in the present invention serves to increase the effectiveness of sterilization rather than to decrease the effectiveness, as in the prior art.

To determine the effect of various pressures on a diffusion restricted sterilization system, the following experiment was performed.

EXAMPLE 6

A stainless steel scalpel blade 5 was placed within a 2.2 cm×60 cm glass tube 20 which was closed at one end, as shown in FIG. 2. Each blade 5 had been inoculated with 1.9×10⁶ B. stearothermophilus spores. To create a diffusion restricted environment, the open end of the glass tube 20 was sealed with a rubber stopper 25 having a 1 mm×10 cm stainless steel tube 30 through its center. Hydrogen peroxide solution at a concentration of 3% was added to the glass tube 20 in amounts of 50, 100, 150 or 200 µl, together with the inoculated blade 5. The tube 20 was placed in a vacuum chamber, and subjected to various pressures for 15 minutes, during which time the temperature increased from approximately 23° C. to approximately 28° C. In a further experiment to determine the effect of increased temperature on the system, the tube 20 was first heated to 45° C., then subjected to 50 Torr pressure for 15 minutes. The results were as follows.

TABLE 6

Effect of Temperature and Pressure on a Diffusion Restricted System

| | 50 µL | 100 µL | 150 µL | 200 µL |
|---|---|---|---|---|
| 15 minutes vacuum with 3% hydrogen peroxide solution: | | | | |
| 1 torr pressure | + | − | − | − |
| 5 torr pressure | − | − | − | − |
| 10 torr pressure | − | − | − | − |
| 15 torr pressure | − | − | − | − |
| 20 torr pressure | − | − | − | − |
| 25 torr pressure | − | − | − | − |
| 30 torr pressure | + | + | + | + |
| 35 torr pressure | + | + | + | + |
| 40 torr pressure | + | + | + | + |
| 45 torr pressure | + | + | + | + |
| 50 torr pressure | + | + | + | + |
| 15 minutes vacuum with 3% hydrogen peroxide at 45° C.: | | | | |
| 50 torr pressure | − | − | − | − |

These data show that sterilization can be achieved in diffusion restricted environments at pressures up to about 25 Torr at 28° C. At pressures of 30 Torr and higher, sterilization was not achieved; this is believed to be due to the fact that the vapor pressure of hydrogen peroxide at 28° C. is approximately 28 Torr. Thus, at higher pressures, the liquid hydrogen peroxide inside the glass tube was not vaporizing. This was confirmed by the testing done at 50 Torr pressure at 45° C., wherein sterilization was achieved. The vapor pressure of hydrogen peroxide is increased at 45° C., thus, the hydrogen peroxide was vaporized at 50 Torr, effectively sterilizing the blade placed inside the tube.

Accordingly, in order to achieve sterilization using the method of the present invention, the temperature and pressure within the vacuum chamber should be such that vaporization of the aqueous hydrogen peroxide solution is achieved, i.e. the system should preferably be operated below the vapor pressure of the hydrogen peroxide. The pressure needs to be below the vapor pressure of hydrogen peroxide, such that the hydrogen peroxide solution present in the system is vaporized and diffuses from the interior of the diffusion restricted environment to the outside. Alternatively, the hydrogen peroxide can be vaporized locally where the system remains above the vapor pressure by introducing energy to the site of the peroxide, such as through microwaves, radio waves, or other energy sources.

To further determine the effect of varying the pressure and the temperature in the diffusion restricted system described in Example 6, the following experiments were performed.

EXAMPLE 7

A stainless steel scalpel blade 5 was placed within a 2.2 cm×60 cm glass tube 20 which was closed at one end, as illustrated in FIG. 2. Each blade 5 had been inoculated with 1.9×10⁶ B. stearothermophilus spores. To create a diffusion restricted environment, the open end of the glass tube 20 was sealed with a rubber stopper 25 having a 1 mm×10 cm stainless steel tube 30 through its center. Hydrogen peroxide solution at a concentration of 3% was added to the glass tube 20 in amounts of 50, 100, 150 or 200 μl together with the inoculated blade 5. The tube 20 was placed in a vacuum chamber, and the chamber evacuated to 5 Torr. To vary the pressure within the chamber, the valve to the vacuum pump was closed, such that the pressure within the chamber rose from 5 Torr to 6.15 Torr after 15 minutes, during which time the temperature increased from approximately 23° C. to approximately 28° C. In a second test, the tube 20 was placed in the chamber and the chamber was evacuated to 50 Torr. The temperature of the glass tube 20 was increased to 45° C. after the evacuation of the chamber was complete. The tube 20 was treated for 15 minutes. The results of these tests are reported below.

TABLE 7

Effect of Varying Temperature and Pressure on Diffusion Restricted Sterilization System

| | 50 μL | 100 μL | 150 μL | 200 μL |
|---|---|---|---|---|
| Pressure increased from 5 Torr to 6.15 Torr: | | | | |
| Efficacy Results | − | − | − | − |
| Temperature of the tube increased to 45° C.: | | | | |
| Efficacy Results | − | − | − | − |

These results show that maintaining a constant pressure or temperature is not required in the diffusion restricted environment to effect sterilization. Under the conditions tested, the hydrogen peroxide is vaporized and kept in contact with the device to be sterilized for a time sufficient to effect complete sterilization.

The method of the present invention relies on the delivery of liquid hydrogen peroxide to the article to be sterilized prior to vacuum or plasma treatment. The following testing was performed to determine the effect of the location of the delivery of the hydrogen peroxide within the diffusion restricted environment.

EXAMPLE 8

A stainless steel scalpel blade 5 was inoculated with $1.9 \times 10^6$ *B. stearothermophilus* spores, and the blade 5 placed in the center piece 10 of a lumen 15 as illustrated in FIG. 1. The dimensions of the center piece 10 were 1.3 cm ID, 5 cm length and 6.6 cc volume, while the lumen itself varied in size, having an ID of 1, 3 or 6 mm, and a length of 15, 27, 40 or 50 cm. The lumen 15 was placed within a 2.2 cm×60 cm glass tube 20. The tube 20 was closed at one end, and the open end was plugged with a rubber stopper 25 having a 1 mm×10 cm stainless steel tube 30 placed through the stopper 25. Thus, gases entering or exiting the glass tube 20 could pass only through this 1 mm×10 cm opening. 10 μl of 3% hydrogen peroxide solution was placed inside the lumen 15, or 100 μl of 3% hydrogen peroxide solution was placed inside the glass tube 20, but outside the stainless steel lumen 15. The glass tube 20 was then placed in a vacuum chamber, which was sealed and evacuated to 1 Torr for 15 minutes, during which time the temperature increased from approximately 23° C. to approximately 28° C. Results of this testing are as follows.

TABLE 8

Effect of Hydrogen Peroxide Solution Placed Outside Inner Lumen

| Peroxide amount | Length | 1 mm ID | 3 mm ID | 6 mm ID |
|---|---|---|---|---|
| 10 μL of 3% in lumen | 50 cm | − | − | − |
| | 40 cm | − | − | − |
| | 27 cm | − | − | − |
| | 15 cm | − | − | − |
| 100 μL of 3% in glass tube | 50 cm | + | + | + |
| | 40 cm | + | + | + |
| | 27 cm | + | + | + |
| | 15 cm | + | + | − |

These data show that, under the test conditions of Example 8, sterilization did not occur within the inner lumen when the hydrogen peroxide solution was placed outside the lumen in a diffusion restricted environment, but that complete sterilization was effected when the hydrogen peroxide solution was placed inside all of the lumens in a diffusion restricted environment. When the hydrogen peroxide vapor must diffuse from outside to inside, the sterilant vapor cannot enter the inner lumen in a diffusion restricted environment unless the lumen is sufficiently large. Thus, when the hydrogen peroxide solution was placed outside the lumen, only the shortest, widest lumens allowed sufficient vapor penetration to allow sterilization inside the lumen. These data confirm that prior art methods which require diffusion of sterilant vapor from outside the article to the interior article cannot achieve sterilization in diffusion restricted environments under these conditions. In contrast, under the same conditions except where the hydrogen peroxide was placed inside the article, allowing hydrogen peroxide to diffuse from inside to outside, complete sterilization occurred with much lower amounts of hydrogen peroxide.

The method of the present invention is therefore useful in environments where diffusion of the sterilant vapor is limited. To evaluate the effect of changes in the amount of diffusion restriction within a diffusion restricted environment, the following testing was performed.

EXAMPLE 9

A stainless steel scalpel blade 5 was inoculated with $1.9 \times 10^6$ *B. stearothermophilus* spores, and placed in a 2.2 cm×60 cm glass tube 20 as illustrated in FIG. 2. The tube 20 was closed at one end, and the open end was plugged with a rubber stopper 25. Stainless steel tubing 30 of various dimensions was inserted through the stopper 25. Thus, gases entering or exiting the glass tube 20 could pass only through the opening in the tubing 30, which varied from 1 mm to 6 mm in diameter. Three percent hydrogen peroxide solution in volumes ranging from 50 μL to 200 μL was also placed inside the glass tube 20. The glass tube 20 was then placed in a vacuum chamber, which was sealed and evacuated to 5 Torr for 15 minutes, during which time the temperature increased from approximately 23° C. to approximately 28° C. In addition, three lumens were tested at 10 Torr for 15 minutes with 3% hydrogen peroxide. The results of this testing are listed below in Table 9.

TABLE 9

Effects of Tubing Dimension and Vacuum Pressure on Sterilization

| SS tubing | 50 µL | 100 µL | 150 µL | 200 µL |
|---|---|---|---|---|
| 15 minutes vacuum at 5 Torr with 3% hydrogen peroxide | | | | |
| 1 mm × 10 cm | – | – | – | – |
| 1 mm × 5 cm | – | – | – | – |
| 1 mm × 2.5 cm | + | – | – | – |
| 3 mm × 10 cm | – | – | – | – |
| 3 mm × 5 cm | – | – | – | – |
| 3 mm × 2.5 cm | + | – | – | – |
| 6 mm × 10 cm | – | – | – | – |
| 6 mm × 5 cm | + | – | – | – |
| 6 mm × 2.5 cm | + | – | – | – |
| 15 minutes vacuum at 10 Torr with 3% hydrogen peroxide | | | | |
| 1 mm × 2.5 cm | – | | | |
| 3 mm × 2.5 cm | – | | | |
| 6 mm × 2.5 cm | – | | | |

Complete sterilization was achieved in the majority of the environments tested. Sterilization could not be achieved at 5 torr using the shortest length of stainless steel tubing and only 50 µl hydrogen peroxide solution. Greater volumes of hydrogen peroxide must be used in these systems.

These data also confirm that the vacuum pressure affects sterilization efficacy, since the container with the shortest and widest exit tube could provide sterilization at 10 Torr, but not at 5 Torr. At too low pressures (such as pressures below 5 Torr in the conditions tested) however, it appears that the hydrogen peroxide vapor is pulled from the interior of the article being sterilized too quickly, resulting in an insufficient amount of hydrogen peroxide vapor being allowed to contact the interior of the device to effect sterilization. It would appear that although a pressure of 5 torr produces acceptable results, a pressure of approximately 10 Torr is better under the conditions tested.

The method of the present invention has been shown to be effective in diffusion restricted environments of metal and glass. To evaluate whether the method is effective in diffusion restricted environments formed of other materials, the experiments described in Examples 10 and 11 were performed.

EXAMPLE 10

For this testing, a diffusion restricted system was tested. $1.2 \times 10^6$ B. stearothermophilus spores were inoculated onto non-woven polypropylene pieces. As illustrated in FIG. 1, the inoculated pieces 5 were placed inside the center piece 10 of a plastic lumen 15, together with 10 µl of 3% hydrogen peroxide solution. The center piece 10 was made of Teflon™ and had dimensions of 1.3 cm×5 cm. The lumen 15 varied from 1 mm to 6 mm ID, and 15 cm to 50 cm in length. Teflon™ was used for the 1 mm lumen, polyethylene was used for the 3 mm and 6 mm lumen. The lumen 15 was then placed within a 2.2 cm×60 cm glass tube 20. The glass tube 20 was closed on one end, and the open end was sealed with a rubber stopper 25 having a 1 mm×10 cm piece of PTFE tubing 30 through it. The glass tube 20 was placed in the vacuum chamber and treated for 15 minutes at 1 Torr, during which time the temperature increased from approximately 23° C. to approximately 28° C. The results of this testing are set forth below.

TABLE 10A

Sterilization in Diffusion Restricted Systems Using Plastic Lumens

| System | Pressure | Length | 1 mm ID | 3mm ID | 6 mm ID |
|---|---|---|---|---|---|
| Diffusion Restricted System | 1 torr | 50 cm | – | – | – |
| | | 40 cm | – | – | – |
| | | 27 cm | – | – | – |
| | | 15 cm | – | – | – |

Sterilization in diffusion restricted environments can be effected in both short, wide lumens and long, narrow lumens, regardless of whether metal or plastic is used to form the lumens. Thus, the method of the present invention is an effective sterilization method for diffusion restricted articles, and can be used on a wide variety of such articles, regardless of their composition.

To further confirm this, $2.1 \times 10^6$ B. stearothermophilus spores were inoculated on stainless steel blades, and $1.2 \times 10^6$ B. stearothermophilus spores were inoculated onto non-woven polypropylene pieces. As shown in FIG. 2, the blades 5 or non-woven polypropylene pieces 5 were placed inside a 2.2 cm×60 cm glass tube 20 together with 50 µl of 3% hydrogen peroxide solution. One end of the tube was closed, and the open end was sealed with a rubber stopper 25 having either a 1 mm×10 cm stainless steel tube 30 therein, or a 1 mm×10 cm piece of Teflon™ tubing 30 therein. The glass tube 20 was placed inside a vacuum chamber and treated for 15 minutes at 5 Torr, during which time the temperature increased from approximately 23° C. to approximately 28° C. The results are as follows.

TABLE 10B

Effect of Metal and Plastic on Sterilization in a Diffusion Restricted System

| | SS tubing | Teflon tubing |
|---|---|---|
| Metal blade | – | – |
| Polypropylene | – | – |

Thus, all four combinations of metal and plastic provide for effective hydrogen peroxide vapor sterilization in a diffusion restricted environment. This testing confirms that the method of the present invention is an effective sterilization method for diffusion restricted articles, and can be used on a wide variety of such articles, regardless of the materials used to form them.

Further testing was next performed to evaluate the effect of various temperatures and pressures on the sterilization of a diffusion restricted system. The testing is described below.

EXAMPLE 11

Stainless steel blades were inoculated with $2.1 \times 10^6$ B. stearothermophilus spores. The blades 5 were placed inside a 2.2 cm×60 cm glass tube 20 as illustrated in FIG. 2, along with various amounts of 3% hydrogen peroxide solution. The glass tube 20 was placed in a vacuum chamber and subjected to different pressures and different temperatures for various periods of time. During the sterilization cycles reported in Table 11A, the temperature increased from approximately 23° C. to the temperatures indicated. In the experiments reported in Table 11B, the chamber was heated to approximately 45° C. In an alternative embodiment, rather than heating the chamber, the temperature of the peroxide solution itself can be heated. In the experiments reported in Table 11C, the temperature increased from approximately 23° C. to approximately 28° C. during the minute period of exposure to vacuum.

TABLE 11A

Effect of Time and Volume of Peroxide on
Sterilization in a Diffusion Restricted Environment

| | 5 min. (approx. 24° C.) | 10 min. (approx. 26° C.) | 15 min. (approx. 28° C.) |
|---|---|---|---|
| At 5 Torr pressure: | | | |
| 50 µL of 3% peroxide | − | − | − |
| 100 µL of 3% peroxide | − | − | − |
| 150 µL of 3% peroxide | + | − | − |
| 200 µL of 3% peroxide | + | − | − |

TABLE 11B

Effect of Elevated Chamber Temperature and Volume of Peroxide on
Sterilization in a Diffusion Restricted Environment

| | 5 min. |
|---|---|
| Chamber at approximately 45° C.: | |
| 150 µL of 3% peroxide | − |
| 200 µL of 3% peroxide | − |

TABLE 11C

Effect of Pressure and Volume of Peroxide on
Sterilization in a Diffusion Restricted Environment

| Approx. 28° C. | 1 torr | 5 torr | 10 torr |
|---|---|---|---|
| With 15 minutes exposure time: | | | |
| 20 µL of 3% peroxide | N/D | + | − |
| 50 µL of 3% peroxide | + | − | − |
| 100 µL of 3% peroxide | − | − | − |

Under the test conditions of Example 11, large volumes of hydrogen peroxide solution were ineffective at achieving sterilization when vacuum was applied for only very short periods of time. This is believed to be at least partially because water vaporizes more quickly than hydrogen peroxide. Thus, the water present in the aqueous solution will vaporize first, and more time is needed to vaporize the hydrogen peroxide. This also explains why the larger volumes of hydrogen peroxide solution were effective at achieving sterilization at higher temperatures; the vaporization of the hydrogen peroxide occurs sooner at higher temperatures. Thus, when more water is present in the system, either higher temperatures or more time is required to achieve sterilization.

Again, it would appear from these data that slightly higher pressures, i.e. 10 Torr, achieve more effective sterilization under these conditions. This is believed to be because at higher pressures, more hydrogen peroxide vapor is retained inside the system. At too low a pressure, the hydrogen peroxide vapor is pulled out of the system too quickly.

In order to evaluate a putative minimum concentration of peroxide in the liquid/vacuum system in a diffusion-restricted container, Example 12 was carried out.

EXAMPLE 12

Various concentrations of peroxide were used in a system substantially as described in connection with FIG. 2. In this system, the exit tube 35 was a stainless steel tube having a length of 50 cm and an internal diameter of 1 mm. A stainless steel blade inoculated with $1.9 \times 10^6$ spores of $B.$ $stearothermophilus$ was placed within the container which was a 2.2 cm×60 cm glass tube. Various amounts of 3% hydrogen peroxide were introduced into the container. The container was placed in a vacuum chamber of 173 liters, and the pressure reduced to 10 Torr for a period of one hour, during which time the temperature increased from approximately 23° C. to approximately 40° C. Sporicidal activity was evaluated at each concentration of peroxide. In addition, the amount of peroxide remaining in the container after the sterilization process was evaluated by standard titration techniques, whereby the peroxide was reacted with potassium iodide and titrated with sodium thiosulfate. Results are shown in Table 12 where "N/D" indicates not determined.

TABLE 12

| Amount of Peroxide in Glass Tube | Sporicidal Activity | Remaining Peroxide |
|---|---|---|
| 0.5 mg/L liquid | + | N/D |
| 0.6 mg/L liquid | + | N/D |
| 0.7 mg/L liquid | + | N/D |
| 0.8 mg/L liquid | + | N/D |
| 0.9 mg/L liquid | + | N/D |
| 1.0 mg/L liquid | − | 0.17 mg/L |

The results reported in Table 12 indicate that 1.0 mg/L of 3% liquid peroxide were required in the system tested to effect sterilization. Further, under the conditions tested, a concentration of 0.17 mg/L of peroxide remaining in the system was sufficient to provide complete sterilization. These data also show that the glass tube used in these experiments provided a sufficient level of diffusion restriction to retain 17% of the hydrogen peroxide placed therein.

We further investigated the effects of length and internal diameter of the exit tube used in a system similar to that of Example 12. This testing is shown in Example 13.

EXAMPLE 13

A system similar to that described above in connection with Example 12, with the exception that 15 minutes of vacuum rather than one hour was used. Thus, the temperature increased only to about 28° C. In this testing, the size of the exit tube 35 was varied, as well as the volume of 3% peroxide solution. The results are reported below in Table 13.

TABLE 13

| | 50 µl | 100 µl | 150 µl | 200 µl |
|---|---|---|---|---|
| Open without tubing | + | + | + | + |
| 6 mm ID × 1 cm length | + | − | − | − |
| 9 mm ID × 1 cm length | + | − | − | − |
| 13 mm ID × 1 cm length | + | + | + | + |

The results show that provided sufficient peroxide is present, the diffusion-restriction provided by a single entry/exit port of 9 mm or less in internal diameter, or 1 cm or greater in length is sufficient to effect sterilization.

To further evaluate the effect on sterilization efficacy of changes in the amount of restriction of vapor diffusion in the system, the following testing was performed.

EXAMPLE 14

A stainless steel blade was inoculated with $2.1 \times 10^6$ $B.$ $stearothermophilus$ spores. The blade 5 was placed inside a 2.2 cm×60 cm glass tube 20 as shown in FIG. 3, together with various amounts of 3% hydrogen peroxide solution. One end of the tube was closed, and the open end was sealed with a rubber stopper 25 having a syringe filter 35 inserted therein. The glass tube 20 was placed inside a vacuum chamber and treated for 15 minutes at 5 Torr, during which time the temperature increased from approximately 23° C. to approximately 28° C. As a control, identically inoculated blades were placed inside 2.2 cm×60 cm glass tubes. The open end of the tubes was left open, no stopper or syringe filter was used. Thus, the diffusion of vapor from the interior of the tube was not restricted.

Various syringe filters having various pore sizes were tested, including MFS PTFE 25 mm syringe filters with a 0.2 μm membrane filter and a 0.5 μm membrane filter; a Nalgene PTFE 50 mm syringe filter with a 0.2 μm membrane filter and a 0.45 μm membrane filter; a Whatman Anotop™ 10 Plus sterile syringe filter with a 0.02 μm membrane filter and a 0.1 μm membrane filter; and finally, a Gelman Acrodisc™ CR PTFE syringe filter with a 0.2 μm, 0.45 μm, and a 1.0 μm membrane. The results are as follows.

TABLE 14

Sporicidal Activity of $H_2O_2$ Solution with Vacuum in a Container Having a Syringe Filter
15 minutes vacuum and 3% hydrogen peroxide:

| | 50 μL | 100 μL | 150 μL | 200 μL |
|---|---|---|---|---|
| (a) Without syringe filter and stopper: | | | | |
| 5 Torr | + | + | + | + |
| 10 Torr | + | + | + | + |
| (b) With MFS ™ PTFE 25 mm syringe filter: | | | | |
| (1) 0.2 μm membrane filter | | | | |
| 5 Torr | + | – | – | – |
| 10 Torr | – | – | – | – |
| (2) 0.5 μm membrane filter | | | | |
| 5 Torr | + | – | – | – |
| 10 Torr | – | – | – | – |
| (3) With 2 MFS ™ filters together at 5 Torr pressure | | | | |
| Two 0.2 μm filters | – | | | |
| Two 0.5 μm filters | – | | | |
| (c) With Nalgene ™ PTFF 50 mm syringe filter: | | | | |
| (1) 0.2 μm membrane filter | | | | |
| 5 Torr | – | – | – | – |
| 10 Torr | – | – | – | – |
| (2) 0.45 μm membrane filter | | | | |
| 5 Torr | – | – | – | – |
| 10 Torr | – | – | – | – |
| (d) With Whatman Anotop ™ 10 Plus syringe filter: | | | | |
| (1) 0.02 μm membrane filter | | | | |
| 5 Torr | – | – | | |
| 10 Torr | – | – | | |
| (2) 0.1 μm membrane filter | | | | |
| 5 Torr | – | – | | |
| 10 Torr | – | – | | |
| (e) With Gelman Acrodisc ™ CR PTFE syringe filter: | | | | |
| (1) 0.2 μm membrane filter | | | | |
| 5 Torr | + | – | | |
| 10 Torr | – | – | | |
| (2) 0.45 μm membrane filter | | | | |
| 5 Torr | + | – | | |
| 10 Torr | – | – | | |
| (3) 1.0 μm membrane filter | | | | |
| 5 Torr | + | – | | |
| 10 Torr | – | – | | |

As is apparent from these results, certain brands of filters do not create a sufficiently diffusion restricted environment at 5 Torr pressure when only 50 μL of hydrogen peroxide solution is placed in the system. Other brands of filters did provide sufficient diffusion restriction; these brands of filters had either longer lumens or smaller filter pore size. Using larger volumes of peroxide solution, 10 Torr pressure, or serial filters enhances the efficacy of the sterilization system. This is important, as filters, including ones made of Tyvek™, are often used in packaging of sterile articles to prevent re-contamination with bacteria. These filters generally have a pore size of 1 μm or less, or in the case of Tyvek™, create a tortuous path which bacteria cannot cross. In the present invention, filters can be used in combination with other packaging means to create a diffusion restricted environment to effect sterilization, and the sterile article can remain inside the packaging during storage prior to use; the filter will prevent re-contamination of the sterile article.

In order to test whether other sterilants can also be used to effect sterilization in diffusion restricted environments, the following testing was performed.

EXAMPLE 15

A stainless steel blade was inoculated with $1.9 \times 10^6$ B. stearothermophilus spores. The blade 5 was placed inside a 2.2 cm×60 cm glass tube 20 as shown in FIG. 2, along with various amounts of 4.74% peracetic acid solution (Solvay Interox Ltd., Warrington, England). The glass tube 20 was placed in a vacuum chamber and subjected to 5 Torr pressure for 15 minutes, during which time the temperature increased from approximately 23° C. to approximately 28° C. The results of this testing is shown below.

TABLE 15

Sterilization With Peracetic Acid in a Diffusion Restricted System

| | 50 μL | 100 μL | 150 μL | 200 μL |
|---|---|---|---|---|
| Efficacy Results | – | – | – | – |

These results show that peracetic acid, in which hydrogen peroxide coexists, can also be used in the sterilization method of the present invention.

It was discovered that by delivering small amounts of hydrogen peroxide solution to an article to be sterilized prior to exposure to vacuum, sterilization could be effected at lower temperatures and in short periods of time. The following testing was performed to evaluate different methods of delivering hydrogen peroxide solution to the article to be sterilized. Further, the efficacy of vacuum treatment and plasma treatment following pretreatment with aqueous hydrogen peroxide were compared. The testing is described in Example 16 below.

EXAMPLE 16

In a first series of tests, stainless steel blades were inoculated with 2.5×10$^6$ *B. stearothermophilus* spores. The blades were placed in the expanded center piece of a 3 mm×50 cm stainless steel lumen. The lumen was placed in a 1000 ml beaker containing 800 ml of hydrogen peroxide solution. The lumen was soaked for 5 minutes in 3% hydrogen peroxide solution. The number of surviving organisms following this initial soak was determined. The lumens were removed from the hydrogen peroxide solution and the outside blotted dry with paper towels. The inside of the lumens were dried by placing one end of the lumen into a flask and blowing with a three second burst of compressed air. The lumens were shaken, and the blowing and shaking repeated until no more solution was blown out. Subsequently, the lumen was placed in a sterilization chamber and exposed to either a vacuum of 0.5 Torr for 15 minutes, or plasma for 15 minutes at 0.5 Torr. After 15 minutes of vacuum, the temperature increased from approximately 23° C. to approximately 28° C. The results are set forth below in Table 16A.

TABLE 16A

Effect of H$_2$O$_2$ Solution Soak on Sporicidal Activity in Stainless Steel Lumens Prior to Either a Plasma or a Vacuum Treatment

| Conc. H$_2$O$_2$ (%) Soak Time 5 min | Number of Surviving Organisms After Soaking Alone | Sterility Test Results | | |
|---|---|---|---|---|
| | | Soak Alone | Soak + Vacuum | Soak + Plasma |
| 3.0 | 8.2 × 10$^5$ | 4/4 | 0/4 | 0/4 |

A five minute soak in 3% hydrogen peroxide solution was an effective means for delivering the hydrogen peroxide into the lumen prior to vacuum or plasma treatment. As noted before, treatment with hydrogen peroxide solution only is ineffective to achieve sterilization using dilute solutions and short soak times. Delivery of hydrogen peroxide solution via static soaking is at least as effective a way to deliver the hydrogen peroxide as depositing small volumes directly into the lumen of the device.

Flow-through delivery of hydrogen peroxide was tested next. Here, stainless steel blades were inoculated with 2.5×10$^6$ *B. stearothermophilus* spores. The blades were placed in the expanded center piece of a 3 mm×50 cm stainless steel lumen. Hydrogen peroxide solution at 3% concentration was delivered to the lumen at a flow rate of 0.1 L/min, using a peristaltic pump. The lumen was dried as described above. Following pretreatment with hydrogen peroxide solution, the lumen was then placed in a sterilization chamber and exposed to either a vacuum of 0.5 Torr for 15 minutes, or plasma for 15 minutes at 0.5 Torr. The results are set forth below in Table 16B.

TABLE 16B

Effects of Flow-Through Delivery of H$_2$O$_2$ Solution on Sporicidal Activity Prior to Either a Vacuum or a Plasma Treatment in Stainless Steel Lumens

| Conc. H$_2$O$_2$ (%) 5 min flow | Number of Surviving Organisms after Flow Alone | Sterility Test Results | |
|---|---|---|---|
| | | Flow + Vacuum | Flow + Plasma |
| 3 | 6.2 × 10$^5$ | 0/4 | 0/4 |

Delivery of the hydrogen peroxide solution via constant flow is also an effective way to deliver hydrogen peroxide to the system.

Finally, the effect of delivery of hydrogen peroxide by aerosol spray was tested. Stainless steel blades were inoculated with 2.5×10$^6$ *B. stearothermophilus* spores. The inoculated blades were placed in the expanded center piece of a 3 mm×50 cm stainless steel lumen. Three percent hydrogen peroxide solution was delivered to the lumen via a 3 second aerosol spray. Aerosol spray rate was determined to be 0.04 L/min. After a 5 minute wait following pretreatment with hydrogen peroxide, the lumen was dried as described above and the lumen was then placed in a sterilization chamber and exposed to either a vacuum of 0.5 Torr for 15 minutes, or plasma for 15 minutes at 0.5 Torr. The results are set forth below in Table 16C.

TABLE 16C

Effects of Aerosol Delivery of H$_2$O$_2$ Solution on Sporicidal Activity Prior to Either a Vacuum or a Plasma Treatment in Metal Lumens

| Conc. H$_2$O$_2$ (%) | Number of Surviving Organisms after Aerosol Alone | Sterility Test Results | |
|---|---|---|---|
| | | Aerosol + Vacuum | Aerosol + Plasma |
| 3 | 7.4 × 10$^5$ | 0/4 | 0/4 |

Flow-through of hydrogen peroxide as either a liquid solution or aerosol can also be achieved by introducing increased pressure at the delivery end or decreased pressure at the exit end of the device to be treated.

It is evident from the data in Tables 16A–16C that all three methods of delivering hydrogen peroxide solution to the article to be sterilized provided for effective sterilization. Thus, it appears that a number of different methods of delivery can be used, as long as the hydrogen peroxide solution is present in the system prior to exposure to vacuum or plasma.

Finally, the efficacy of pretreatment with hydrogen peroxide prior to a sterilization cycle which combines exposure to hydrogen peroxide vapor, vacuum, and plasma was evaluated. The testing was as follows.

EXAMPLE 17

Stainless steel blades were inoculated with 2.5×10$^6$ *B. stearothermophilus* spores. The blades were soaked in 3% hydrogen peroxide solution for either 1 or 5 minutes. The blades were then placed in the expanded center piece of a 3 mm×50 cm stainless steel lumen. The lumen was then placed in a sterilization chamber which was evacuated to approximately 0.5 Torr. The sterilization cycle consisted of 15 minutes of hydrogen peroxide vapor diffusion with a minimum of 6 mg/L hydrogen peroxide, followed by 15 minutes of plasma at 400 watts. Following the plasma treatment, the chamber was vented and the blades tested for sterility. The results are shown below.

TABLE 17

Effects of $H_2O_2$ Solution Soak on Sporicidal Activity in Stainless Steel Lumens Prior to a Hydrogen Peroxide Vapor and Plasma Cycle

| | | Sterility Test Results | |
|---|---|---|---|
| Conc. $H_2O_2$ | Soak Time | Soak Alone | Soak + Cycle |
| 3% | 1 min | 4/4 | 0/4 |
| | 5 min | 4/4 | 0/4 |

Processing the lumens in a hydrogen peroxide vapor and plasma cycle alone left an average of 30 surviving organisms per blade. Pretreating the blades by soaking in 3% hydrogen peroxide solution for 5 minutes alone left an average of $8.2 \times 10^5$ surviving organisms per blade. Thus, under the test conditions, a combination of hydrogen peroxide vapor exposure and plasma exposure, which has been found to be effective for many articles, was ineffective in a diffusion restricted environment. However, by pretreating the article to be sterilized with dilute hydrogen peroxide solution prior to exposure to hydrogen peroxide vapor and plasma, complete sterilization can be achieved.

While the invention has been described in connection with liquid sterilant solutions containing hydrogen peroxide, it will be appreciated by those having ordinary skill in the art that equivalent sterilization methods can be adapted for other sterilant liquids. In an alternative embodiment, a sterilant having a vapor pressure lower than that of water or other solvent in which the sterilant is provided is used. For such sterilants, it is only important that the vapor pressure be lower than that of the solvent within the temperature ranges contemplated herein. Such sterilants can be adapted for the techniques described herein with only minor adjustments made for the differences in vapor pressure between peroxide and such other sterilant, as can be readily determined by those having ordinary skill in the art. As long as the local vapor pressure at the site of the sterilant liquid is below the vapor pressure of the sterilant, sterilization can be achieved substantially as described hereinabove.

CONCLUSION

Achieving rapid sterilization of lumened devices at low temperatures using low concentrations of sterilants has, until now, been exceedingly challenging. A superior method of sterilization has been discovered which overcomes the problems of the known methods. By pretreating articles to be sterilized with an aqueous solution of hydrogen peroxide prior to exposure to a vacuum, rapid sterilization can be achieved at low temperatures, without damage to the articles, without leaving toxic residues behind, and without the need to attach special vessels. The method of the present invention is efficient, nonhazardous, and inexpensive as well.

What is claimed is:

1. A method for sterilizing an interior of a device having a lumen, comprising:

contacting the interior of said lumen with a liquid solution comprising hydrogen peroxide; and exposing said device to a selected negative pressure and a selected temperature to vaporize said hydrogen peroxide, wherein said lumen has a length and diameter which provide the same or more diffusion restriction than provided by a reference lumen 27 cm in length and having an internal diameter of 3 mm, at said selected pressure and said selected temperature, and wherein said hydrogen peroxide vapor diffuses from inside to outside of said lumen, for a time period sufficient to effect sterilization of said lumen by hydrogen peroxide vapor.

2. The method of claim 1, wherein said liquid solution is an aerosol.

3. The method of claim 1, wherein said solution is peracetic acid.

4. The method of claim 1, wherein said contacting step comprises delivery of said liquid solution via one or more methods selected from the group consisting of injection, static soak, liquid flow-through and aerosol spray.

5. The method of claim 1, wherein the lumen of said device is at least 27 cm in length and has an internal diameter of no more than 1 mm.

6. The method of claim 1, further comprising exposing said device to a plasma while exposing the device to negative pressure.

7. The method of claim 6, wherein said method is performed within a first chamber and wherein said plasma is generated in a second, separate chamber and said method further comprises the step of flowing said plasma into said first chamber.

8. The method of claim 6, wherein said method is performed within a sealed chamber and said plasma is generated within said chamber.

9. The method of claim 1, wherein if the exposing step is conducted at 40° C. and 10 torr for one hour and if in the contacting step 1 mg of hydrogen peroxide per liter of lumen volume is introduced into said lumen, said lumen is sufficiently diffusion restricted to retain a concentration of 0.17 mg or more hydrogen peroxide per liter of lumen volume, wherein 0.17 mg/L is the total concentration of hydrogen peroxide liquid at 1 atmosphere pressure, remaining after the exposing step.

10. The method of claim 1, wherein if the exposing step is conducted at 40° C. and 10 torr for one hour and if in the contacting step 1 mg of hydrogen peroxide per liter of lumen volume is introduced into said lumen, said lumen is sufficiently diffusion restricted to retain 17% or more of the total hydrogen peroxide introduced therein after the exposing step, wherein the 17% is the hydrogen peroxide liquid at 1 atmosphere pressure, remaining after the exposing step.

11. The method of claim 1, wherein the contacting step is repeated one or more times.

12. The method of claim 1, wherein the exposing step is repeated one or more times.

13. The method of claim 1, wherein both the contacting step and the exposing step are repeated one or more times.

14. The method of claim 1, wherein said solution is at a concentration of less than 25% by weight.

15. The method of claim 1, wherein said exposing step is performed for 60 minutes or less.

16. The method of claim 1, further comprising the step of heating said device during said exposing step.

17. The method of claim 1, wherein said exposing step occurs within a chamber, and wherein said method further comprises the step of heating said chamber during said exposing step.

18. The method of claim 17, wherein said chamber is heated to between about 40° C. and about 45° C.

19. The method of claim 1, additionally comprising heating said solution prior to said contacting step.

20. The method of claim 19, wherein said solution is heated to between about 40° C. and about 45° C.

21. The method of claim 1, wherein said exposing step comprises exposing said device to pressure less than the vapor pressure of hydrogen peroxide.

22. The method of claim 21, wherein said pressure is between 0 and 100 torr.

23. The method of claim 22, wherein said pressure is approximately 10 torr and the exposing step is conducted at a temperature of approximately 23° C. to approximately 28° C.

24. A method for sterilizing an interior and an exterior of an article having a lumen, comprising:

contacting the interior of said lumen with a liquid solution comprising hydrogen peroxide; and placing said article in a diffusion-restricted environment, said contacting and placing steps being performed in either order; followed by exposing said diffusion-restricted environment to a selected negative pressure and a selected temperature to vaporize said hydrogen peroxide for a time period sufficient to effect sterilization of the interior and exterior of said article by hydrogen peroxide vapor, wherein said lumen has a length and diameter which provide the same or more diffusion restriction than provided by a reference lumen 27 cm in length and having an internal diameter of 3 mm, at said selected pressure and said selected temperature.

25. The method of claim 24, wherein the contacting step is performed before the placing step.

26. The method of claim 25, additionally comprising contacting the article with a liquid solution comprising hydrogen peroxide again after the placing step.

27. The method of claim 24, additionally comprising heating said solution prior to said contacting step.

28. The method of claim 24, wherein said exposing step occurs within a chamber, and wherein said method further comprises the step of heating said chamber during said exposing step.

29. The method of claim 24, wherein if the exposing step is conducted at 40° C. and 10 torr for one hour and if in the contacting step 1 mg of hydrogen peroxide per liter of lumen volume is introduced into said lumen, said diffusion restricted environment is sufficiently diffusion restricted to retain 17% or more of the total hydrogen peroxide placed therein after the exposing step, wherein the 17% is the hydrogen peroxide liquid at one atmosphere pressure, remaining after the exposing step.

30. The method of claim 24, wherein if the exposing step is conducted at 40° C. and 10 torr for one hour and if in the contacting step 1 mg of hydrogen peroxide per liter of lumen volume is introduced into said lumen, said diffusion restricted environment is sufficiently diffusion restricted to retain a concentration of 0.17 mg or more hydrogen peroxide after the exposing step per liter of lumen volume wherein said 0.17 mg/L or more hydrogen peroxide is the total concentration of hydrogen peroxide liquid at one atmosphere pressure, remaining after the exposing step.

31. The method of claim 24, wherein said solution is peracetic acid.

32. The method of claim 24, wherein said contacting step comprises delivery of said liquid solution via one or more methods selected from the group consisting of injection, static soak, liquid flow-through and aerosol spray.

33. The method of claim 24, further comprising exposing said article to a plasma while exposing the article to negative pressure.

34. The method of claim 33, wherein said method is performed within a first chamber and wherein said plasma is generated in a second, separate chamber and said method further comprises the step of flowing said plasma into said first chamber.

35. The method of claim 24, wherein said diffusion-restricted environment comprises a container with at least one exit tube.

36. The method of claim 35, wherein said exit tube is at least 1.0 cm in length.

37. The method of claim 35, wherein said exit tube has an internal diameter of 9 mm or less.

38. The method of claim 35, wherein said exit tube includes a filter.

39. The method of claim 38, wherein said filter is sufficient to prevent entry of bacteria from the environment into said container.

40. The method of claim 24, wherein said solution is at a concentration of less than 25% by weight.

41. The method of claim 24, wherein said exposing step is performed for 60 minutes or less.

42. The method of claim 24, further comprising the step of heating said article during said exposing step.

43. The method of claim 24, wherein said exposing step comprises exposing said article to negative pressure between 0 and 100 Torr.

44. The method of claim 24, wherein the contacting step is repeated one or more times.

45. The method of claim 24, wherein the exposing step is repeated one or more times.

46. The method of claim 44, wherein the entire method is repeated one or more times.

47. The method of claim 24, wherein said diffusion-restricted environment has the same or more diffusion restriction than provided by a single entry/exit port of 9 mm or less in internal diameter and 1 cm or greater in length.

48. The method of claim 24, wherein said diffusion-restricted environment is sufficiently diffusion restricted to completely sterilize a stainless steel blade within a 2.2 cm by 60 cm glass tube having a rubber stopper with a 1 mm by 50 cm stainless steel exit tube therein at a vacuum of 10 torr for one hour at 40° C.

49. A method for sterilizing a device having a lumen, comprising:

contacting the interior of said lumen with a liquid solution comprising hydrogen peroxide; and exposing said device to a selected negative pressure and a selected temperature to vaporize said hydrogen peroxide, wherein said lumen has a length and a diameter which provide the same or more diffusion restriction than provided by a reference lumen having a length to internal diameter ratio of 50 at said selected pressure and said selected temperature, and wherein said hydrogen peroxide vapor diffuses from inside to outside of said lumen, for a time period sufficient to effect sterilization of said lumen by hydrogen peroxide vapor.

50. The method of claim 49, wherein said liquid solution is an aerosol.

51. The method of claim 49, wherein said solution is peracetic acid.

52. The method of claim 49, wherein said contacting comprises delivery of said liquid solution via one or more methods selected from the group consisting of injection, static soak, liquid flow-through and aerosol spray.

53. The method of claim 49, further comprising exposing said device to a plasma while exposing the device to negative pressure.

54. The method of claim 53, wherein said method is performed within a first chamber and wherein said plasma is generated in a second, separate chamber and said method further comprises flowing said plasma into said first chamber.

55. The method of claim 53, wherein said method is performed within a sealed chamber and said plasma is generated within said chamber.

56. The method of claim 49, wherein the contacting is repeated one or more times.

57. The method of claim 49, wherein the exposing is repeated one or more times.

58. The method of claim 49, wherein both the contacting and the exposing are repeated one or more times.

59. The method of claim 49, wherein said solution is at a concentration of less than 25% by weight.

60. The method of claim 49, wherein the exposing is performed for 60 minutes or less.

61. The method of claim 49, further comprising heating said device during said exposing.

62. The method of claim 49, wherein said exposing occurs within a chamber, and wherein said method further comprises heating said chamber during said exposing.

63. The method of claim 62, wherein said chamber is heated to between about 40° C. and about 45° C.

64. The method of claim 49, additionally comprising heating said solution prior to said contacting.

65. The method of claim 64, wherein said solution is heated to between about 40° C. and about 45° C.

66. The method of claim 49, wherein said exposing comprises exposing said device to pressure less than the vapor pressure of hydrogen peroxide.

67. The method of claim 66, wherein said pressure is between 0 and 100 torr.

68. The method of claim 66, wherein said pressure is approximately 10 torr and the exposing is conducted at a temperature of approximately 23° C. to approximately 28° C.

* * * * *